United States Patent [19]

Harandi et al.

[11] Patent Number: 5,002,915

[45] Date of Patent: Mar. 26, 1991

[54] PROCESS FOR CATALYST REGENERATION WITH FLUE GAS

[75] Inventors: Mohsen N. Harandi, Lawrenceville; Hartley Owen, Belle Mead, both of N.J.

[73] Assignee: Mobil Oil Corp.

[21] Appl. No.: 358,095

[22] Filed: May 30, 1989

[51] Int. Cl.[5] ...................... B01D 29/38; B01D 38/16; C10G 51/06; C07C 2/12

[52] U.S. Cl. ........................................ 502/51; 208/78; 208/79; 502/38; 502/41; 502/49; 585/531; 585/533

[58] Field of Search ...................... 502/38, 49, 51, 52, 502/41; 208/78, 79, 84, 85, 164

[56] References Cited

U.S. PATENT DOCUMENTS

| | | | |
|---|---|---|---|
| 2,278,509 | 4/1942 | Brown | 252/242 |
| 2,391,327 | 12/1945 | Mekler | 252/242 |
| 2,845,409 | 7/1958 | Pennington et al. | 260/93.1 |
| 2,905,622 | 9/1959 | McCarthy | 208/78 |
| 3,046,235 | 7/1962 | King et al. | 252/411 |
| 3,960,978 | 6/1976 | Givens et al. | 260/683.15 R |
| 4,456,779 | 6/1984 | Owen et al. | 585/415 |
| 4,542,114 | 9/1985 | Hegarty | 502/39 |
| 4,822,477 | 4/1989 | Avidan et al. | 208/164 |
| 4,867,950 | 9/1989 | Harandi et al. | 422/190 |

FOREIGN PATENT DOCUMENTS

| | | | |
|---|---|---|---|
| 554927 | 3/1958 | Canada | 208/79 |

*Primary Examiner*—Paul E. Konopka

[57] ABSTRACT

A process for regenerating solid particulate catalyst used in fixed bed hydrocarbon conversion processes, such as the shape selective zeolite conversion of olefins to gasoline and diesel fuel. Regeneration is achieved using a portion of a flue gas stream to regenerate catalyst and preheat feedstock. Economies in equipment and operation are realized by employing a once-through configuration for the regenerator gas stream.

3 Claims, 2 Drawing Sheets

PROCESS FOR CATALYST REGENERATION WITH FLUE GAS

REFERENCE TO COPENDING APPLICATION

This application is related to U.S. Pat. application Ser. No. 107,709 filed 13 Oct. 1987, now U.S. Pat. No. 4,867,950 incorporated herein by reference.

BACKGROUND OF THE INVENTION

This invention relates to a process for regenerating the catalysts used in fixed bed hydrocarbon catalytic conversion.

The reaction of hydrocarbon feedstocks in the presence of catalysts to produce gasoline range products, diesel fuels, aromatics, or other valuable fuels and chemicals is frequently carried out using fixed catalyst beds at elevated temperature. These catalyst beds require periodic regeneration of the catalyst, commonly conducted by contacting the catalyst with an oxygen-containing gas at elevated temperature in order to remove by combustion those coke and carbonaceous deposits responsible for the deactiviation of the catalyst. For continuous fixed bed catalytic processes, the process design generally incorporates at least two fixed bed catalyst reactors which are sequentially or alternately operated as a regenerator vessel or process vessel such that the catalyst is undergoing oxidative regeneration in one vessel while the alternate or "swing" vessel is converting the hydrocarbon feedstock to the desired product.

In these processes provision is routinely made for the recirculation of the regeneration gas stream which requires recompression of the gas, makeup air compressor controls, filters and heat exchangers as needed to reconstitute the regenerator gas stream and recycle that stream under the precise conditions of temperature, pressure and composition needed to oxidatively remove the deleterious carbonaceous deposits on the catalyst. Examples of processes which use oxidative catalyst regeneration involving fixed bed swing reactors include reforming, catalytic hydrodesulfurization, catalytic dehydrogenation, the methanol-to-gasoline processes (MTG), and olefins, upgrading such as the olefins oligomerization processes to produce gasoline and distillate hydrocarbons.

To facilitate control of gas composition, the flue gas generally used for regeneration is recycled. Prior techniques, such as U.S. Pat. No. 2,391,327 to Meckler, discloses processes for the regeneration of solid contact material used for promoting hydrocarbon conversion reactions using flue gas where the flue gas is generated in a regenerator gas combuster, recycled through heat exchange zones and filters and incorporates instrumentation to sense and adjust the composition of chemicals in the flue gas to the preferred ratios. Such treatment requires a significant investment in capital equipment and can be the source of inefficiencies in the overall process. Regenerator gas cycles also require substantial capital investment for heat exchange, recycle gas compression and chemical composition control in order to provide a recycle flue gas stream suitable for use in catalyst regeneration.

The added costs and inefficiencies incurred in the course of providing a suitable recycle flue gas stream have presented a substantial problem and challenge to workers in the field of fixed bed catalyst regeneration.

It has been discovered that an available flue gas can be employed as the catalyst regenerating gas stream in a once through configuration consolidating flue gas and regenerating gas treatment steps. In particular, the process of this invention used available flue gas heat to preheat feedstock and oxidatively regenerate catalyst. It is a main object of the present invention to provide a process for the oxidative regeneration of catalysts employed in a fixed bed hydrocarbon conversion processes that is efficient and economically advantageous without requiring recycle of the regenerator gas stream. It is another object of this invention to provide a process for the regeneration of fixed bed catalytic hydrocarbon conversion processes by combining available flue gas streams with catalyst regeneration in an efficient and economically advantageous configuration.

Yet another object of the present invention is to combine the catalyst regeneration of fixed bed hydrocarbon conversion processes with the catalyst regenerator operations of a fluid catalytic cracking process in a manner so as to achieve maximum utilization of commonly useful equipment and the energy resources in the FCC catalyst regenerator flue gas stream.

SUMMARY OF THE INVENTION

The objects of the present invention are achieved in a process using an available flue gas stream, such as from an oxidative catalyst regeneration zone of the catalyst regenerator vessel of a fluid catalytic cracking process, to provide heat to generate steam or preheat the feed stream to the process reactor of a fixed bed catalyst conversion process, such as a Mobil olefin-to-gasoline and diesel process, then to oxidatively regenerate the catalyst in a fixed bed catalyst regenerator. Following these steps the flue gas streams are combined and treated in the flue gas cooler and electrostatic precipitator before discharging to the atmosphere without recycling.

The foregoing process is accomplished by first withdrawing a portion of the FCC flue gas stream and adjusting the composition of that stream to provide an oxidizing flue gas stream essentially free of FCC catalyst fines useful for catalyst regeneration. The portion so withdrawn is partially cooled by generating steam or heat exchange with the feedstock stream to the fixed bed hydrocarbon conversion process reactor. Then the heated hydrocarbon feedstock stream is passed to the process reactor over active catalyst particles under such conditions as necessary to convert the feedstock stream to hydrocarbon products which are then separated. A portion of the partially cooled oxidizing flue gas stream, after partial cooling, is contacted with deactivated catalyst having carbonaceous deposits thereon in the swing or alternate catalyst oxidative regenerating reactor for a process such as olefins upgrading.

The effluent gas stream from the catalyst regenerating reactor is combined with the remaining portion of partially cooled oxidizing flue gas stream and the undiverted portion of the flue gas stream. The combined streams are cooled in the flue gas cooler, treated to remove particulates and discharged to the atmosphere, without recycling.

Adjusting the composition of the portion of the flue gas stream, such as from the FCC regeneration zone, to provide an oxidizing flue gas stream is accomplished by mixing the stream with air, nitrogen or fuel gas as required to provide an appropriate oxidizing stream composition. The air stream for such mixing is further provided by air from the main air blower outlet employed in connection with providing combustion air for the FCC oxidative catalyst regeneration zone.

DESCRIPTION OF THE PREFERRED EMBODIMENTS

One preferred embodiment of the present invention involves the integration of the catalyst oxidative regenerator operation of a fluid catalytic cracking reactor with a hydrocarbon fixed bed catalytic conversion process such as the catalytic olefins-to-gasoline and distillate process (sometimes called MOGD). Fluid catalytic cracking is a process well known in the art requiring no further elaboration or explanation herein.

Figure 2:
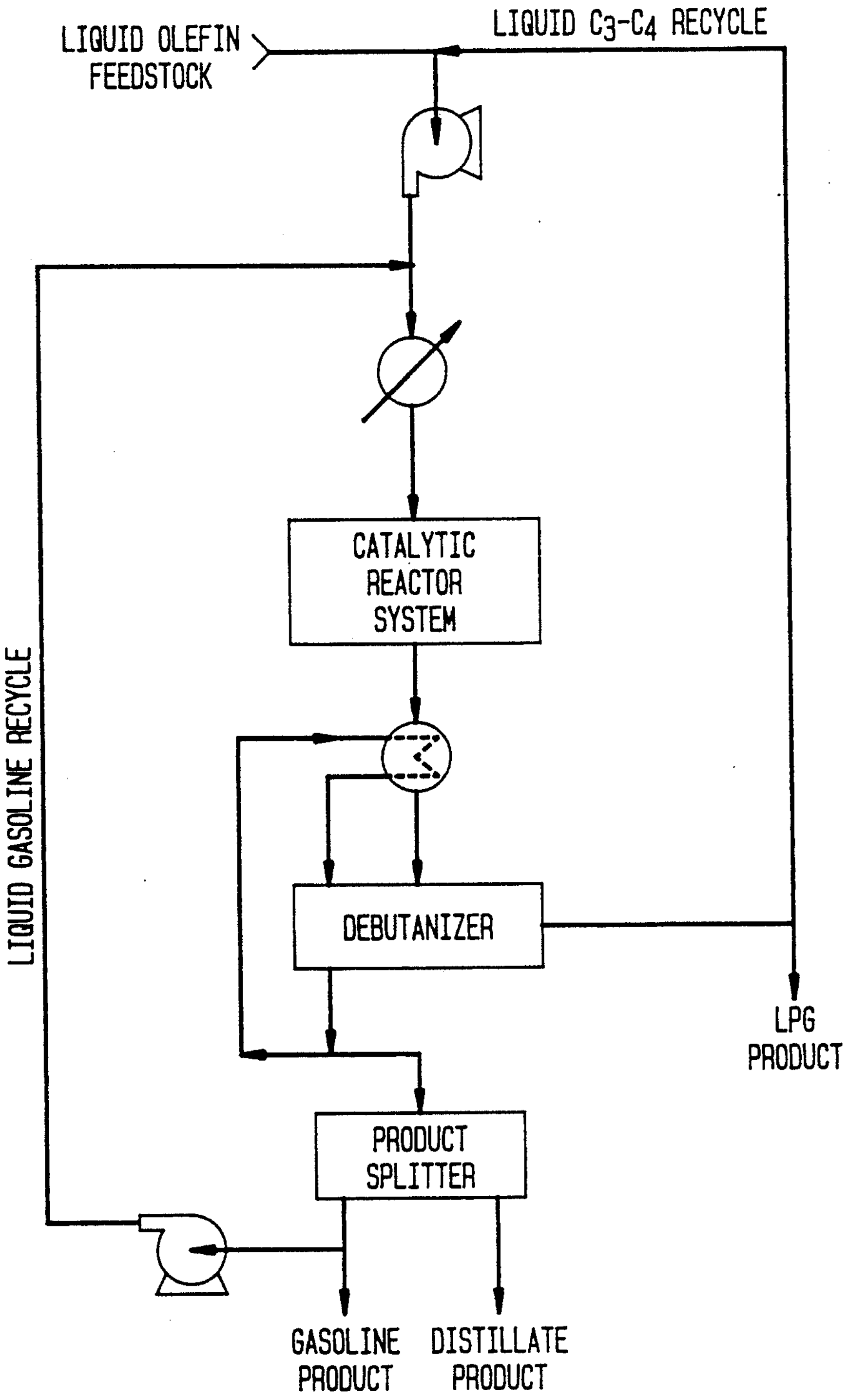
FIG. 2 is a schematic diagram showing the olefin upgrading process configuration.

For olefin upgrading, the flow diagram of FIG. 2 of the drawing represents the overall process. The olefinic feedstock is usually supplied as a liquid stream under moderate superatmospheric pressure and warm ambient temperature. Ordinarily, the feedstock is substantially below the process reactor pressure, and may be combined with recycled liquid diluent which may be rich in olefinic gasoline or $C_3$–$C_4$ alkanes at similar temperature and pressure. Following pressurization of the combined olefin-recycle and/or gasoline feedstreams, it may be passed through the catalytic reactor system, which includes multiple fixed bed reactors operatively connected with the heat exchange system, as described later. The reactor effluent may be cooled by heat exchange with a debutanizer bottoms fraction. A condensed debutanizer overhead stream is recovered for recycle and the heavier hydrocarbons obtained by oligomerization of the feedstream are fractionated in a product splitter unit to yield a $C_{10}^+$ distillate fraction (330° F.+boiling point) and a $C_5$–$C_9$ gasoline fraction (boiling range of 125° F. to 330° F.) in varying amount.

Since the gasoline product comprises a major fraction of unsaturated aliphatic liquid hydrocarbons, it may be recovered and hydrotreated to produce spark-ignited motor fuel if desired. Optionally, all or a portion of the olefinic gasoline range hydrocarbons from the splitter unit may be recycled for further conversion to heavier hydrocarbons in the distillate range. This may be accomplished by combining the recycle gasoline with lower olefin feedstock and diluent prior to heating the combined streams.

Process conditions, catalysts and equipment suitable for use in the oligomerization process are described in U.S. Pat. Nos. 4,456,799 (Owen et al.), 3,960,978 (Givens et al.), 4,021,502 (Plank et al.), and 4,150,062 (Garwood et al.). The above disclosures are incorporated herein by reference.

Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, or Fe, within the zeolitic framework. These medium pore zeolites are favored for acid catalysis; however, the advantages of ZSM-5 structures may be utilized by employing highly siliceous materials or crystalline metallosilicate having one or more tetrahedral spaces having varying degrees of acidity. ZSM-5 crystalline structure is readily recognized by its X-ray diffraction pattern, which is described in U.S. Pat. No. 3,702,866 (Argauer, et. al.), incorporated by reference.

The acidic medium pore zeolite-type catalyst materials suitable for use in the MOGD process are effective in oligomerizing lower olefins, especially propene and butene to higher hydrocarbons. The unique characteristics of acid ZSM-5 catalyst are particularly suitable for use in the MOGD system. Other members of the class of zeolites for use in MOGD are exemplified by ZSM-5/ZSM-11, ZSM-11, ZSM-12, ZSM-23, ZSM-35, ZSM-38, ZSM-48 and other similar materials.

Figure 1:
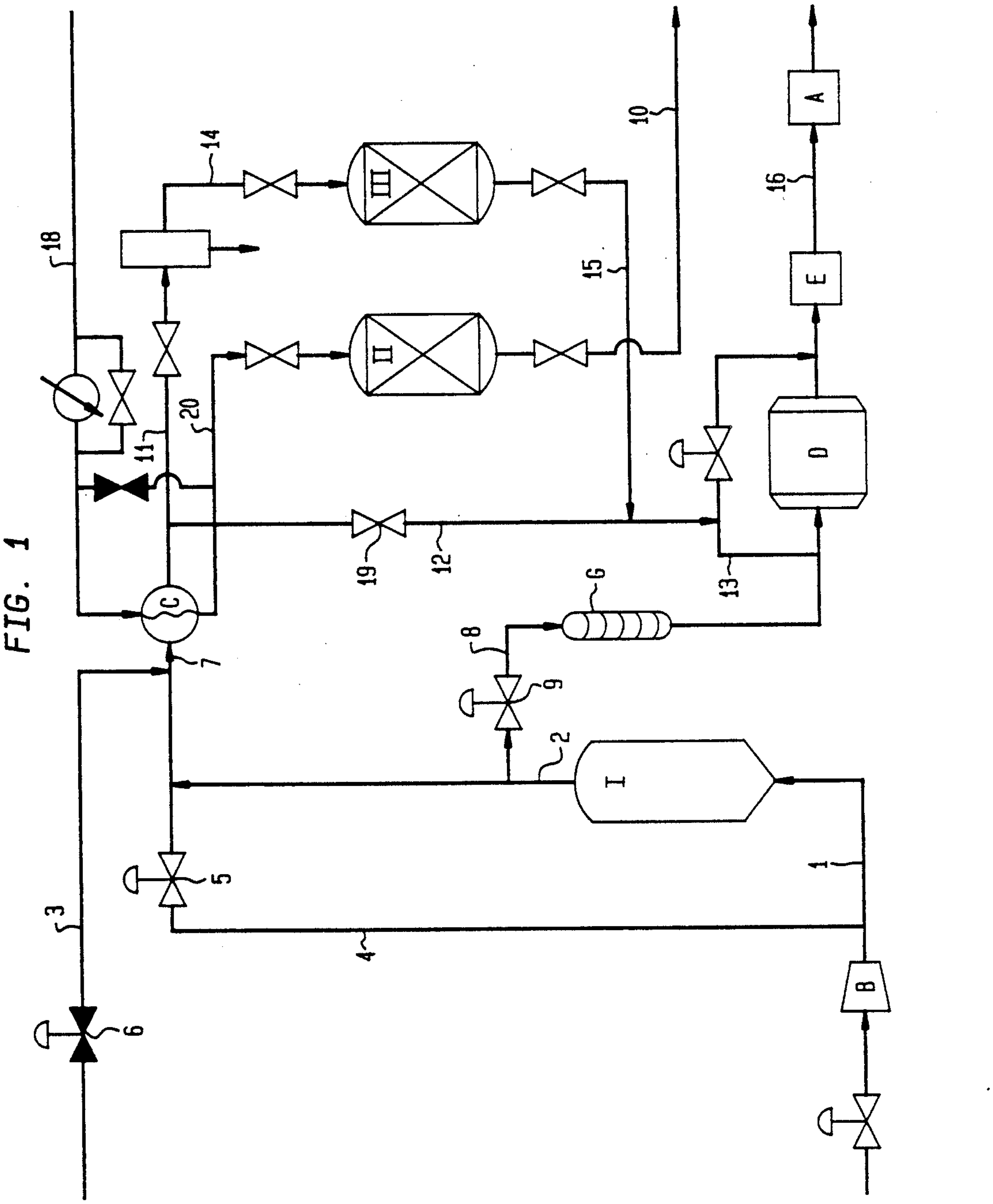
FIG. 1 is a process flow diagram illustrating the integration of FCC regenerator flue gas with the catalyst regeneration section of a olefin-to-gasoline and diesel upgrading process.

Referring to FIG. 1, a process flow diagram of a preferred embodiment of the instant invention is presented. The diagram illustrates the utilization of a flue gas taken from the catalyst regenerator of a fluid catalytic cracking unit as it is employed as the regenerator gas stream for an MOGD process converting olefins to gasoline using dual fixed bed catalytic reactors which alternate as process reactor or catalyst regenerating reactor. The alternate or swing mode of operation for fixed bed reactors is controlled by values 21–28 and operatively connected conduits 29–32 in a known manner. In FIG. 1, (I) is the fluid catalytic cracking regenerator wherein catalyst is received for oxidative regeneration from the cracking unit through conduits not shown. Combustion air is supplied to the unit through conduit 1 from the FCC regenerator air compressor B. As it is passed in contact with hot circulating catalyst in the regenerator vessel (I), the combustion air burns off coke and carbonaceous deposits on the catalyst and exits the reactor through conduit 2 generally at a temperature between 1100° and 1450° F., but preferably about 1350° F. and a pressure between 20 and 40 psig, but preferably about 30 psig. Typically the composition of the exiting flue gas is low with respect to oxygen as a result of the combustion reaction and consists primarly of nitrogen, carbon dioxide and carbon monoxide. In addition to the aforementioned components, the flue gas contains substantial amounts of water vapor representing about 10 volume percent of the flue gas. The water partial pressure in the flue gas is about 3–5 psia. If required the water partial pressure can be reduced to about 1 psia by cooling the flue gas and removing the condensed water before using the flue gas for fixed bed regeneration.

The composition of the flue gas exiting the FCC regenerator through conduit 2, to the extent that it is depleted in oxygen and enriched in reducing gases such as carbon monoxide, departs from the preferred composition of a catalyst regeneration gas useful for the oxidative regeneration of catalysts used in fixed bed hydrocarbon conversion processes. To burn off carbonaceous deposits on those catalyst, a regenerator gas stream with a useful oxygen content is required. Therefore, in the instant invention, a provision is made to modify the composition of the flue gas either through dilution with nitrogen, or addition of fuel gas, such as refinery gas, to reduce oxygen content, through conduit 3 or by the addition of air through conduit 4 as provided from the FCC regenerator air compressor unit B. Under flue gas conditions, the addition of fuel gas thereto results in auto-ignition, consuming oxygen to an appropriate, predetermined concentration. Suitable valves and controls 5 and 6 are included to achieve the compositional changes as may be required in the flue gas.

Conventionally, the flow of flue gas exiting an FCC catalyst regenerator through conduit 2 is substantially in excess of the amount of gas that is required as a source of regenerator gas for fixed bed catalytic hydrocarbon conversion processes, particularly when the oxygen content of that gas has been augmented with air from the FCC air compressor. Further, the total flue gas flow cannot exceed the maximum pressure drop that can be tolerated through the MOGD regenerator system. Therefore, excess flue gas is sent 8 through the FCC flue gas processing system consisting of pressure control valve 9, orifice chamber G, flue gas cooler D, electrostatic precipitator E and stack A.

That quantity of FCC regenerator flue gas not required as a source of MOGD catalyst regenerator gas is withdrawn through conduit 12 and associated valving 19 and passed to an FCC flue gas cooler while a typically minor portion of said flue gas is treated as described heretofore and constituted as a regenerator gas at a temperature between 1100° and 1450° F. but preferably about 1350° F. and a pressure of 20 to 40 psig but preferably 30 psig. The FCC flue gas derived regenerated gas stream is passed by conduit 7 into a heat exchanger C to generate steam or for indirect heat transfer to the MOGD process feed stream entering the heat exchanger through conduit 18. Before entering the MOGD regenerator, particulates are removed from the flue gas stream, typically by filtration.

In the process side MOGD reactor (II) the olefinic feedstock, passed by conduit 20, is contacted with a fixed bed zeolite-type catalyst to produce predominantly gasoline or distillate products under the conditions described in the aforenoted referenced patents. The predominantly gasoline and/or distillate products are carried from the reactor by conduit 10, processed by heat exchange and separation techniques to produce the products as also described in the aforenoted referenced patents.

Regenerator gas derived from flue gas exits heat exchanger C through conduit 11 at a temperature between 700° to 1000° F. and a pressure between 15 and 35 psig but preferably about 25 psig. That volume of flue gas derived regenerator gas in excess of the amount required for zeolite catalyst regeneration is passed through conduit 12 to bypass the swing reactor operating in a catalyst regeneration mode and into conduits 13 and 8 to the FCC flue gas cooler D.

The flue gas derived regenerator gas passing through conduit 11 is filtered and passed through the regenerator reactor (III) through conduit 14 at a temperature preferably about 700° F.-950° F. and a pressure preferably about 23 psig. Zeolite catalyst in the fixed bed regenerator reactor is then regenerated under oxidative regeneration conditions as described in the aforenoted referenced patents. The regenerator gas effluent stream is passed from the reactor through conduit 15 and to the FCC flue gas cooler through conduit 13 where the consolidated or combined flue gas and regenerator gas streams are cooled, electrostatically treated to remove suspended particles in the electrostatic precipitator E and conducted to stack A through conduit 16 for discharge to the atmosphere.

A surprising discovery of the instant invention is that the nitrogen compounds typically present in flue gas do not permanently poison MOGD catalyst as regenerated herein. It is known that nitrogen compounds, such as ammonia, deactivate by adsorbtion on the catalyst, but when the regenerator temperature is raised to about 950° F. nitrogen compounds are desorbed and catalyst activity is regained, as practiced herein.

A key element of the present invention is the adaptability of FCC regenerator flue gas for use as a catalyst regenerator gas for catalytic hydrocarbon conversion processes such as MOGD. In particular, it is well know that zeolite-type catalysts used in such fixed bed hydrocarbon conversion processes as MOGD are sensitive to the water partial pressure in the regenerator gas stream. It is also well known that water vapor can react with zeolite catalyst hydrothermally during regeneration to substantially alter catalyst activity and render the catalyst less effective for the intended conversion reaction.

In view of this deleterious affect of water vapor on the catalyst during catalyst regeneration it is a surprising discovery that FCC regenerator flue gas can be used as catalyst regenerator gas since that flue gas typically contains approximately 10 volume % water. However, in the preferred practice of the instant invention water is not removed from flue gas prior to introduction to the catalyst regenerator. It has been discovered that the invented once through regeneration system pressure is several times lower than the conventional recirculating regeneration system pressure. Therefore, the invented regeneration system can tolerate several times higher water concentration in the regenerator gas.

Another distinguishing aspect of the present invention is the utilization of FCC regenerator flue gas to preheat the olefinic feedstock stream to the alternate process side reactor, resulting in a considerable advantage in energy conservation. The preheating step typically is conducted following the treatment of the FCC regenerator flue gas with nitrogen or air to provide an oxidative regenerator gas stream. However, to those skilled in the art it is obvious that the sequence of these steps may be reversed.

Of particular advantage in the present invention is the discovery of the dual adaptability of elements of the FCC regenerator process to dual usage with MOGD catalyst regeneration and the compatibility of FCC flue gas with a once through design for zeolite catalyst regeneration. Substantial savings in the cost of a typical commercial MOGD plant are realized by eliminating the regeneration recycle gas compressor, the make-up air compressor, several heat exchangers and other vessels that are required as part of a conventional MOGD regeneration process design.

FCC equipment elements that are used in a dual function include the FCC regenerator main air blower, the FCC flue gas cooler and all of the associated stack gas clean-up equipment. In addition, the FCC flue gas is advantageously used as a heat souce to generate steam or preheat the MOGD olefinic feedstock.

While the novel system of the present invention has been described by reference to a particular embodiment, there is no intent to limit the inventive concept except as set forth in the following claims.

We claim:

1. A continuous, once through process using a hot flue gas stream from a fluid catalytic cracking catalyst regenerator to regenerate deactivated zeolite catalysts having carbonaceous deposits thereon in catalytic conversion processes employing multiple fixed bed reactors operatively connected for sequential conversion and catalyst regeneration, comprising:

(a) withdrawing a first portion of said hot flue gas stream to provide an oxidizing flue gas stream containing a substantial amount of water;

(b) partially cooling said oxidizing flue gas stream by indirect heat exchange to preheat the catalytic conversion process feedstock stream;

(c) contacting the heated feedstock with active zeolite catalyst under conversion conditions in a first fixed bed reactor to produce hydrocarbon products;

(d) separating said hydrocarbon products;

(e) contacting a particulate free first portion of step (b) partially cooled, oxidizing flue gas stream containing a substaintial amount of water at a temperature between about 700° to 1000° F. and a pressure of between about 15 to 35 psig with deactivated zeolite catalyst having carboneous deposits thereon in a second fixed bed reactor under catalyst oxidative regenerating conditions at a temperature substantially lower than said fluid catalytic cracking catalyst regenerator;

(f) cooling the consolidated streams comprising the effluent gas streams from said second reactor, the remaining portion of step (e) partially cooled oxidizing flue gas stream and the remaining portion of step (a) hot flue gas stream; and (g) discharging said cooled consolidated streams without recycling.

2. A process according to claim 1 wherein step (a) first portion of hot flue gas stream is mixed with air, inert gases or fuel gas in amounts sufficient to provide an oxidizing flue gas stream comprising between 0.1 and 1.5 volume % oxygen.

3. A process according to claim 1 wherein step (a) oxidizing flue gas stream temperature is between 1100° to 1450° F. with a pressure of 20 to 40 psig.

* * * * *